United States Patent
Mao et al.

(10) Patent No.: US 6,368,277 B1
(45) Date of Patent: Apr. 9, 2002

(54) DYNAMIC MEASUREMENT OF PARAMETERS WITHIN A SEQUENCE OF IMAGES

(75) Inventors: Zuhua Mao; Peng Jiang, both of Issaquah; Patrick L. Von Behren, Bellevue; David E. Gustafson, North Bend, all of WA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/543,030

(22) Filed: Apr. 5, 2000

(51) Int. Cl.[7] .................................................. A61B 8/00
(52) U.S. Cl. ........................................................ 600/441
(58) Field of Search ................................. 600/437, 440, 600/441, 443, 447, 449, 450, 454, 455, 407; 73/625, 626; 367/7, 11

(56) References Cited

U.S. PATENT DOCUMENTS 5,873,830 A * 2/1999 Hossack et al. ............ 600/447
5,971,927 A * 10/1999 Mine ........................... 600/455
6,152,878 A * 11/2000 Nachtomy et al. .......... 600/467
6,193,660 B1 * 2/2001 Jackson et al. ............. 600/443

* cited by examiner

Primary Examiner—Marvin M. Lateef
Assistant Examiner—Ali M. Imam

(57) ABSTRACT

A method of dynamically measuring parameters within a series of images using image processing is disclosed. A sequence of ultrasound images is generated by means of an ultrasound system. A user determines at least one region of interest within a first image. Then, at least one parameter for each region of interest is evaluated, e.g. the number of pixels exceeding a pre-defined intensity are counted. A new region of interest within a sequential image is searched within a search area around the predefined region of interest which best matches the region of interest. This is done for all images of a sequence whereby the new region of interest which best matches the region of interest of the previous image is used as a region of interest for the following image.

20 Claims, 3 Drawing Sheets

DYNAMIC MEASUREMENT OF PARAMETERS WITHIN A SEQUENCE OF IMAGES

BACKGROUND OF THE INVENTION

The present invention relates to a technique for accurately displaying information received, e.g., by means of Doppler mode and/or B-mode while tracking the movements of the particular object or objects, e.g. a blood vessel, which is exposed to the Doppler measurement. In clinical examinations it is often necessary to determine the amount of blood flowing through one or more blood vessels or specific organs. Clinical evidence has shown that there are certain relations between the pathological status of an organ and the time history of the blood flow through the organ. To determine the amount of blood flowing through an organ or blood vessel, usually such a contrast agent may be employed to improve the detection by means of the well-known Doppler technique and/or B-mode techniques. However, organs and blood vessels tend to move within the body and therefore a dynamic measurement particularly in real-time is difficult to obtain and can easily be falsified due to the movement.

SUMMARY OF THE INVENTION

It is therefore an object of the present invention to provide a method and apparatus to overcome this problem. According to the present invention gray scale image region tracking is used to generate a sequential B-mode and/or Doppler-mode intensity signal. These graphs may be displayed as a parametric image. The disclosed technique can be used for one or more regions of interest selected by a user. The regions can be as small as a single pixel, though image comparison routines provide greater confidence for large objects. The disclosed technique is applicable with or without the use of a contrast agent.

A first method of dynamically measuring parameters within a series of images comprises the steps of:

receiving a sequence of images determining at least one region of interest within a first image, evaluating at least one parameter within said region of interest and displaying said parameters, searching within a sequential image a search area around said predefined region of interest which best matches said region of interest, repeating said evaluation and search for said sequence of images.

Another method of dynamically measuring parameters within a series of images using image processing, comprises the steps of:

a) receiving a sequence of ultrasound images, b) determining at least one region of interest within a first image, c) evaluating at least one parameter for each region of interest, d) searching a new region of interest within a sequential image a search area around said predefined region of interest which best matches said region of interest, e) repeating steps c) to d) for all images whereby said new region of interest which best matches said region of interest is used as new region of interest for the following image.

An embodiment of an ultrasound imaging system for dynamically measuring parameters within a series of images using image processing comprises means for generating a sequence of images. Furthermore, input means for determining at least one region of interest within a first image are provided. Also, means for evaluating at least one parameter within said region of interest, and processing means for searching a new region of interest within a sequential image which search a search area around said predefined region of interest which best matches said region of interest are provided.

DETAILED DESCRIPTION OF THE INVENTION

Figure 1:
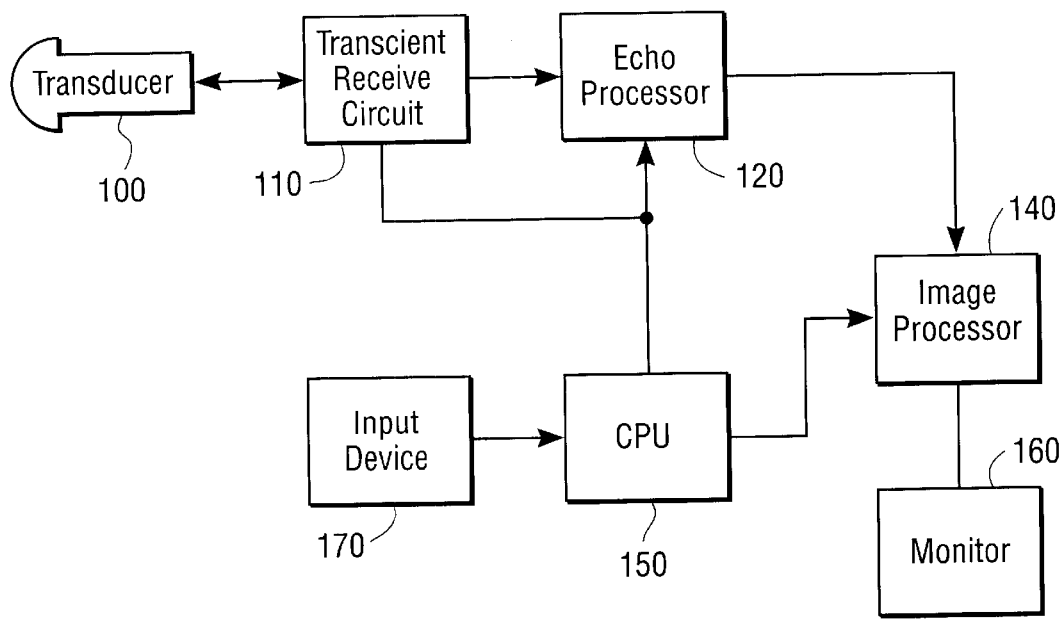
FIG. 1 shows a block diagram of an embodiment of the present invention.

FIG. 1 is a block diagram of an ultrasound system that produces sequential images of an object of interest and comprises a transducer. The ultrasonic transducer 100 comprises an array of piezoelectric crystals that deliver ultrasonic energy into a patient and receive ultrasonic echoes from the patient. Electrical signals representative of the echoes produced by the transducer 100 are delivered to transmit/receiver unit 110 where they are selectively combined to produce an indication of the echo intensity along a particular direction or beam in the patient. The data produced by the transmit/receiver unit 110 are fed to an echo processor 120 that calculates an echo parameter at each position along a beam. The echo processor may incorporate a beam former and may scan convert the data parameters. Furthermore, the echo processor may calculate a Doppler shift, the power of a Doppler shift, the echo intensity of a fundamental, the echo intensity of all non-linear components, the echo intensity of harmonic or sub-harmonic components, the strain, attenuation or thermal properties, etc. of the echoes received along a particular beam. Data from the echo processor 120 is fed to a scan converter 130 that converts the data into a form that can be readily displayed on a video monitor. This arrangement generates a series of images with a specified frame rate.

The data produced by the scan converter is stored in an image processor 140, for example, on a hard drive, where an additional processing, such as adding color, may be performed prior to displaying the images on a video monitor 160. The image processor may include one or more processor sub-systems including digital signal processors (DSPs) and/or general purpose processors for further enhancement and/or processing. Controlling the operation of the above-referenced parts are one or more central processing units 150. The central processing units 150 also receive commands from a user through a variety of controls (not shown) that allow the user to adjust the operation of the ultrasound machine. A light pen, trackball, a mouse input device 170 or any other input device is coupled with the central processing unit 150 to allow a user to define specific points of interest on the screen 160. The system can further be equipped with a voice recognition system to activate and/or control features of the present invention.

Figure 2:
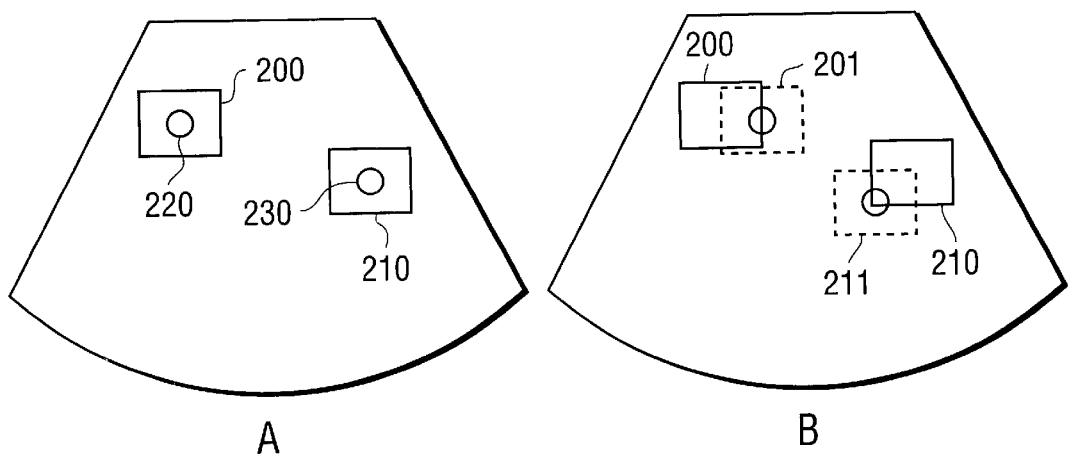
FIG. 2 shows a first image setup and a second image after tracking according to the present invention.

FIG. 2A shows a typical set up screen. Firstly, a sequence of ultrasound images using the B-mode and/or Doppler-mode of the global region within, e.g. a patient is taken. Therefore, ultrasound waves are sent via the transducer 100 into a body and are reflected by tissue, organs, etc. The reflected waves are processed within the echo processor 120 and further processed by scan converter 130 and image processor 140 to form a visual image of the examined area. A series of images with a predefined frame rate can be stored, e.g. on a hard disk or processed in real-time. Secondly, the user defines in a setup screen that displays a first image of an image series or the initial scan in case of a real-time operation one or more regions of interest (ROI) by means of an input device 170, such as a mouse, a light pen, a graphic tablet, touch screen, etc. In FIG. 2A, e.g. two ROI 200 and 210 have been defined. The ROIs according to FIG. 2 have a square or rectangular shape. Within these pre-defined ROI 200 and 210 lie, e.g. a blood vessel or a specific organ or part of an organ. The region of interest can have a square, rectangular, circular, elliptic, polygon or user-defined shape. A user can choose which shape is the most appropriate for the respective region of interest. Size and shape may depend on the respective object of interest. Regions of interest (ROI) are placed in the Doppler or B-mode image over selected vasculature. The signal intensity is measured from the image by summing the image values (Doppler or B-mode) in the ROI. Graphs of the ROI values over time are plotted to demonstrate the time history of the blood flow. Parameters derived from the graphs may be used to quantitate blood flow.

Now follows the evaluation of the pre-defined ROIs. Therefore, each ROI is examined by an examination routine. Within this routine, for example a threshold for B-mode images is set. The routine then counts every pixel within the ROI whose intensity exceeds the pre-defined threshold. In another embodiment multiple parameters within one ROI can be determined by a plurality of ranges. If certain characteristics lie within a specific intensity range, different parameters can be separated by different intensity ranges. To define an intensity range multiple registers can store the respective range values. The registers can be hardware registers or can be represented by specific memory locations within the main memory of the image processor. To enhance the echos sent back from the examined blood vessel or organ, in addition contrast agents may be used. Furthermore, different methods of image processing can be applied. For example, instead of using the fundamental echo waves for gray-scale intensity imaging, the so-called harmonic imaging technique can be used. Especially contrast agents reflect ultrasound waves with harmonics which can be filtered out to distinguish them from tissue reflections which have less or no harmonics. Another method is called the phase inversion method that uses two ultrasound waves with an inverted phase. Thus, the reflected ultrasound waves are combined to eliminate or minimize the fundamental component of the received signal and only the remaining non-linear components contribute to the images sent to the image processor. If a Doppler-mode is used with or without the B-mode, usually the Doppler-mode results are displayed in color on the screen to distinguish it from the B-mode picture. In this case the routine counts the colored pixels within the ROI indicating the amount of blood and/or contrast agent within a blood vessel or organ. Again, multiple parameters can be separated by means of different intensity ranges if appropriate. The result of this evaluation can be depicted in a graph, for example, at the bottom of the screen.

As a next step, the evaluation of the image series is started. For each following image in the sequence it is first evaluated whether the ROI 200 and 201 have moved. FIG. 2B shows a sequential ultrasound image with moved ROI 201 and 211. The calculation of the new ROIs can be done by means of an image comparison routine. A suitable method is described in U.S. Pat. No. 5,575,286 which is hereby incorporated by reference. For example, a search area around the ROI of a first image is defined and a best match within this search area of the second image is calculated and establishes a new ROI. The new ROIs will be used for the following ultrasound image, etc. In the shown example of FIG. 2B the object, e.g. the blood vessel or organ, would have moved out of the initial ROI and therefore without the method according to the present invention a false evaluation would have taken place. FIG. 2B is an exaggerated display of a movement of an object which could actually occur over time, in other words over a series of images.

A suitable image comparison routine, for example, defines a search area around a ROI. The ROI may have the size of N pixel points in lateral direction and M pixel points in axial direction for the first B-mode image. As mentioned above, any kind of shape, such as polygon, circular, etc. can be established for a ROI. The search regions will be defined for the succeeding image with the size of N+2δN pixel points in lateral direction and M+2δM pixel points in axial direction for the second B-Mode image. The following search will be done for each ROI at 2δN by 2δM locations. At each location, a sum-absolute-difference (SAD) value is computed, whereby each SAD ROI has M×N points. The SAD value is evaluated for each (I,j) until a minimum of SAD occurs which will be the best match of the respective ROI of the first and second image. These values also represent the new ROI for a following image and new values are calculated in the same manner for all following images of a series. The respective equation may be represented by:

$$SAD(i, j) = \sum_{n=1}^{N} \sum_{m=1}^{M} \|I_{m,n} - J_{m+i,n+j}\|$$

where I and J are the grade levels (B-mode image intensities) at the user specific locations from these two B-mode images. The parameters I and J are within the following ranges: $-\delta n <= I <= \delta n$, $-\delta m <= j <= \delta m$. The displacements in both lateral and axial directions are given by X1=id and Y1=jd, whereby d is the image pixel size. This result of this coarse-scale search is usually precise enough for the purpose of tracking a specific pre-defined area containing, e.g. a blood vessel or organ. For ideal cases, where noise signals are relatively small compared to the echo signals, the accuracy of this search is mainly limited by the pixel size of the B-image. For example, using a 2.5PL20 probe for cardiac imaging in vivo with a depth of 80.0 mm, the pixel size is about 0.17 mm, which is much smaller than other uncertainties caused by other artifacts, such as the variation of speed of sound or the organs complex motion.

Instead of the sum-absolute-difference method (SAD) a sum square difference (SSD), or a cross correlation method or any other suitable image comparison can be used. Also all methods can also be used as normalized methods.

Figure 3:
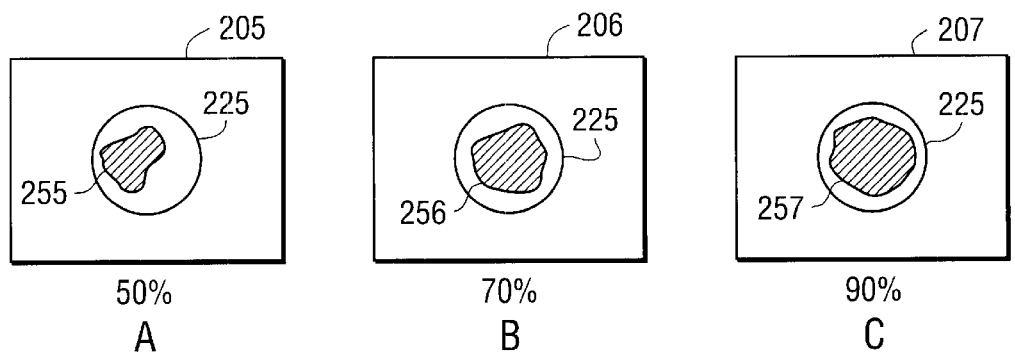
FIG. 3 shows an image sequence using Doppler-mode according to the present invention.
Figure 4:
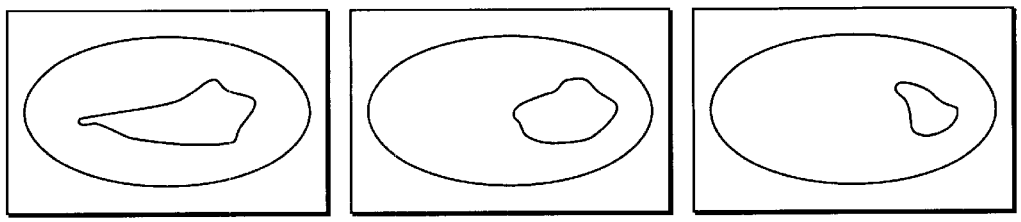
FIG. 4 shows an image sequence using B-mode according to the present invention.
Figure 5:
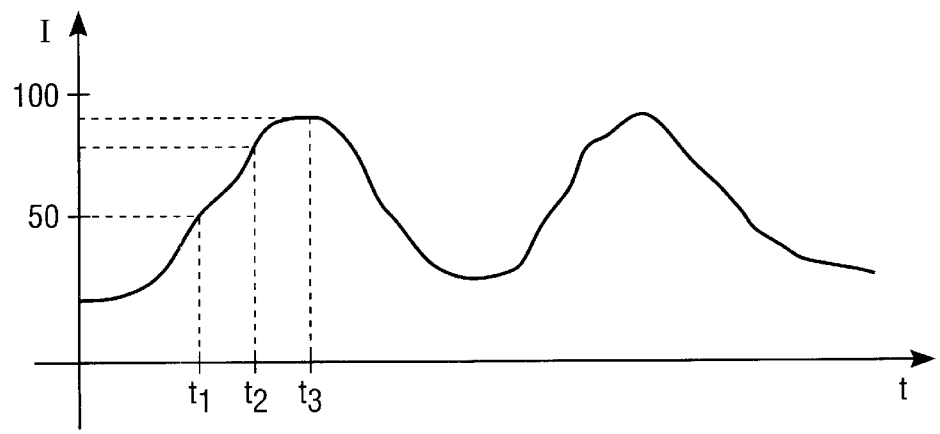
FIG. 5 shows a resulting graph achieved by the method according to the present invention.

Once the new ROIs are established the evaluation routine as described above takes place again to determine, for example the amount of blood and/or contrast agent in the respective investigated object. The resulting data will again be displayed in the above-mentioned graph. FIG. 5 shows a sample graph for a fully computed image sequence. The shown graph represents a time intensity parametric curve. Multiple regions are represented by different graphs (only one shown in FIG. 5). In addition, certain characteristic parameters, such as rise time, decay time, peak value of the curve can be displayed to give further information to a user. Many other parametric values are possible. FIG. 3 shows an example of a series of three ROIs 205, 206, and 207 taken out of an ultrasound image sequence. In this example the B-mode is combined with Doppler-mode, wherein the result of the Doppler-mode is overlayed in color on top of the B-mode image. The color is represented by shaded areas 255, 256, and 257. It represents the amount of blood/contrast agents flowing through object 225, e.g. a blood vessel. The different ROIs 205, 206, and 207 represent different stages within a series of ultrasound images taken, for example as shown in FIG. 5 at times t1, t2, and t3, respectively. FIG. 4 shows a similar sequence of ROIs of an ultrasound image sequence applying the B-mode. In this sequence a pre-defined threshold is set by a user. The threshold separates the object of interest, e.g. blood, contrast agent, etc. from other representations, such as tissue, bones, etc. The ROI evaluation routine will count the pixels whose brightness level is above the pre-defined threshold and display it in a similar manner as described a with respect to FIG. 3.

Figure 6:
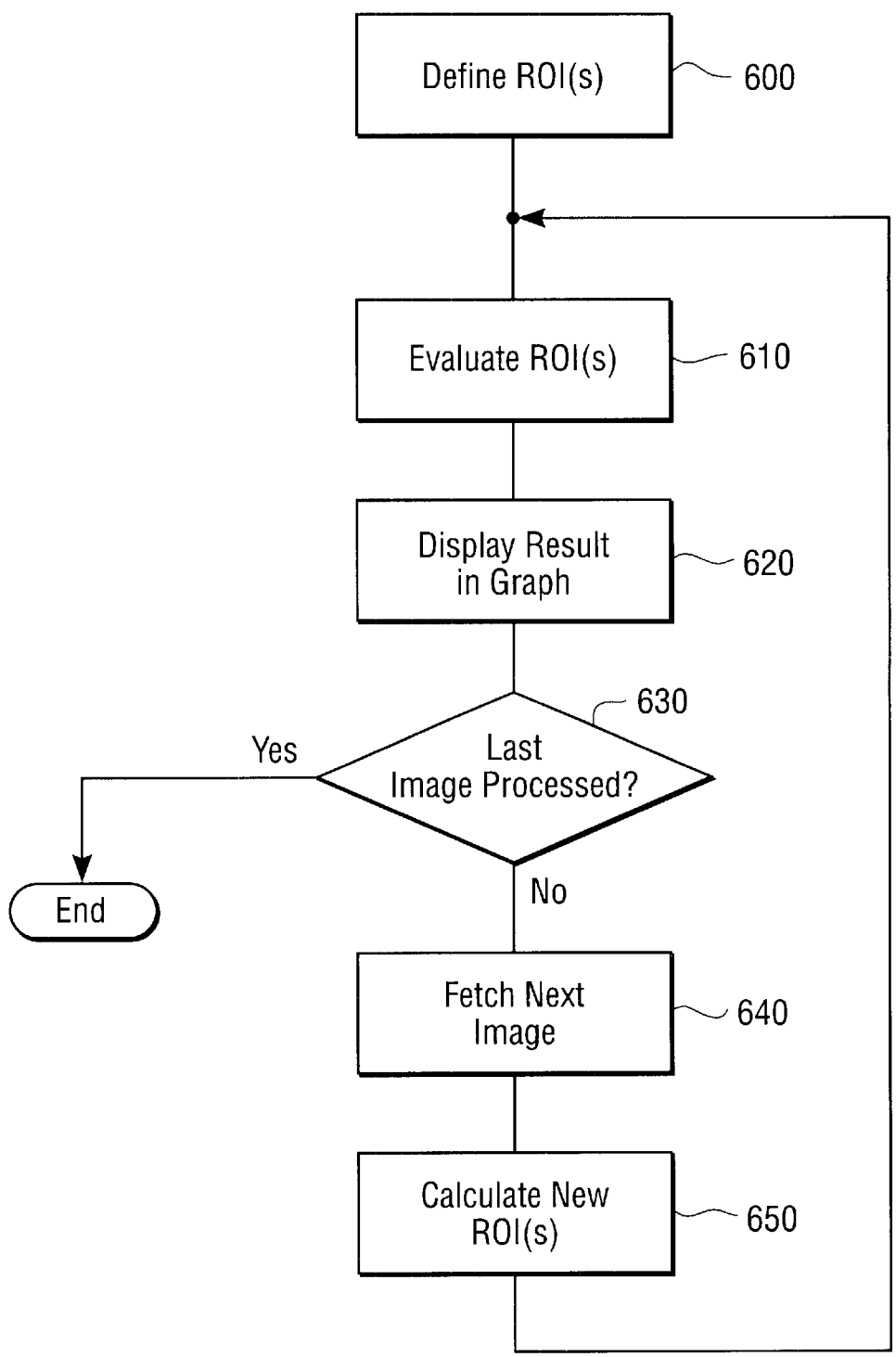
FIG. 6 shows a first flow chart of the method according to the present invention.

FIG. 6 depicts a flow chart diagram showing a typical evaluation of an ultrasound image series according to the present invention. After an image sequence has been recorded one or more ROIs are defined by a user in step 600. In step 610 one or more ROIs are evaluated as described above and in step 620 the results are stored and/or displayed. Step 630 determines whether the last image of an ultrasound image has been processed. If yes, the routine ends, if no, then the next image of the ultrasound image sequence is fetched in step 640. In step 650 one or more new ROIs are calculated and the routine repeats step 610-650 until the whole sequence has been processed.

The method according to the present invention is also not limited to the described post-processing. Instead, a real time application is easily feasible. After the ultrasound transducer has been placed on, e.g. the patient by one hand, the user defines the ROI(s) either before or after the collection of the image sequence., for example, by means of a light pen or mouse operated with his other hand. Once the ROI(s) have been defined the method according to the present invention keeps track of the ROI(s) and the graph (FIG. 5) can be displayed in real-time.

Furthermore the tracking can be performed in a forward time direction or in a reverse mode. Also, if suitable an image within a sequence may be deleted or skipped from consideration or edited if the motion is too large. In another embodiment, if the tracking algorithm does not identify the ROI in a specific image of the sequence it can automatically skip this image. The threshold value for skipping an image, or in other words the quality of a specific image may be defined by a user. Furthermore, if an automatic image match is not found with the search algorithm, a user can manually define a region location. This method is in particular suitable within any kind of post-processing.

Any type of image comparison technique can be applied in step 650. For example, a certain preferably static characteristics, such as a static shape or brightness transitions can be vectorized and its position can be compared in the following images thus defining reference coordinates which are used to define the position of the ROIs. As described any type of blood flow imaging technique such as Doppler-mode, harmonic-mode, phase-inversion-mode, etc. can be used to provide proper data for the evaluation of a ROI. Any type of image comparison technique which is able to track an object is applicable. The present invention is not limited to the use of ultrasound and can also be applied to any type of ultrasound, radiology or MR system.

The present invention avoids any motion effect on the accuracy of an estimation of a time intensity curve.

What is claimed is:

1. Method of dynamically measuring parameters within a series of images comprising:

receiving a sequence of images;

determining at least one region of interest within a first image;

evaluating at least one parameter within said region of interest, the parameter being a function of a first type of information;

displaying said at least one parameter;

searching within a sequential image a search area which best matches said region of interest, the searching being a function of a second type of information, the second type of information different than the first type of information; and repeating said evaluation and search for said sequence of images.

2. Method according to claim 1, wherein said search is done by means of image comparison.

3. Method according to claim 1, wherein said image is an ultrasound image in B-mode.

4. Method according to claim 1, wherein said image is an ultrasound image in a combined B-mode and Doppler-mode.

5. Method according to claim 4, wherein said parameter is the number of pixels within said region of interest generated by said Doppler-mode.

6. Method according to claim 1, wherein said parameter is the number of pixels having a brightness exceeding a pre-defined threshold.

7. The method of claim 1 wherein evaluating at least one parameter comprises calculating an amount of blood from Doppler information and searching comprises searching B-mode information.

8. The method of claim 1 wherein evaluating at least one parameter comprises calculating an amount of contrast agent from Doppler information and searching comprises searching B-mode information.

9. Method of dynamically measuring parameters within a series of images using image processing:

a) receiving a sequence of ultrasound images;

b) determining at least one region of interest within a first image;

c) evaluating at least one blood or contrast agent parameter for each region of interest;

d) searching B-mode intensities within a sequential image a search area around said predefined region of interest which best matches said region of interest; and e) repeating steps c) to d) for all images wherein a new region of interest which best matches said region of interest is used as a new region of interest for the following image.

10. Method according to claim 9, wherein said search is done by means of image comparison.

11. Method according to claim 9, wherein said image is an ultrasound image in B-mode.

12. Method according to claim 9, wherein said image is an ultrasound image in a combined B-mode and Doppler-mode.

13. Method according to claim 12, wherein said parameter is the number of pixels within said region of interest generated by said Doppler-mode.

14. Method according to claim 13, wherein said parameter is the number of pixels having a brightness exceeding a pre-defined threshold.

15. Method according to claim 9, wherein said parameter is displayed.

16. The method of claim 9 wherein evaluating at least one blood or contrast agent parameter comprises calculating the blood or contrast agent parameter as a function of Doppler-mode information.

17. Ultrasound imaging system for dynamically measuring parameters within a series of images using image processing:

means for generating a sequence of images;

input means for determining at least one region of interest within a first image;

means for evaluating at least one parameter within said region of interest and a new region of interest, the at least one parameter being a function of Doppler mode information; and processing means for searching B-mode information for the new region of interest within a sequential image which best matches said at least one region of interest.

18. Ultrasound imaging system according to claim 17, further comprising means for performing a Doppler-mode, wherein said evaluation means comprise counting means to determine the number of pixels generated by said Doppler-mode.

19. Ultrasound imaging system according to claim 17, wherein said evaluation means comprise counting means and means to set up a threshold, said counting means counting the pixels within said region of interest having an intensity exceeding said threshold.

20. Ultrasound imaging system according to claim 17, wherein said evaluation means further comprise a plurality of registers storing at least one intensity range and wherein said counting means count the number of pixels within said region of interest having an intensity within said range.

* * * * *